(12) United States Patent
Son et al.

(10) Patent No.: US 7,595,055 B2
(45) Date of Patent: Sep. 29, 2009

(54) **PHARMACEUTICAL COMPOSITION COMPRISING AN EXTRACT OR COMPOUNDS ISOLATED FROM *ELFVINGIA APPLANATA* FOR THE PREVENTION AND THE TREATMENT OF DIABETES AND DIABETIC COMPLICATIONS**

(75) Inventors: Dal-Hoon Son, #7933, Mount Carmel BLVD., Niagara Falls Ontario, Ontario (CA) L2H 2Y1; Sung-Soon Son, #7933, Mount Carmel BLVD., Niagara Falls Ontario, Ontario (CA) L2H 2Y1

(73) Assignees: Dal-Hoon Son, Ontario (CA); Sung-Soon Son, Ontario (CA)

( * ) Notice: Subject to any disclaimer, the term of this patent is extended or adjusted under 35 U.S.C. 154(b) by 307 days.

(21) Appl. No.: 10/543,912

(22) PCT Filed: Mar. 3, 2003

(86) PCT No.: PCT/KR03/00411

§ 371 (c)(1),
(2), (4) Date: Jul. 28, 2005

(87) PCT Pub. No.: WO2004/067009

PCT Pub. Date: Aug. 12, 2004

(65) Prior Publication Data

US 2007/0224213 A1      Sep. 27, 2007

(30) Foreign Application Priority Data

Jan. 29, 2003  (KR) ............. 10-2003-0005776
Jan. 29, 2003  (KR) ............. 10-2003-0005777
Jan. 29, 2003  (KR) ............. 10-2003-0005778
Jan. 29, 2003  (KR) ............. 10-2003-0005779

(51) Int. Cl.
*A61K 36/09* (2006.01)
*C12N 1/00* (2006.01)
*A61K 31/56* (2006.01)

(52) U.S. Cl. ............. 424/195.15; 435/254.1; 514/178

(58) Field of Classification Search ............. None
See application file for complete search history.

(56) References Cited

FOREIGN PATENT DOCUMENTS

| | | |
|---|---|---|
| EP | 0 411 624 A2 | 2/1991 |
| JP | 59-001426 | 1/1984 |
| JP | 62-234028 | 10/1987 |
| JP | 2000-063281 | 2/2000 |
| JP | 2002-068994 | 3/2002 |
| WO | WO 91/19731 | 12/1991 |

OTHER PUBLICATIONS

Jun Hee Cheon, et al., "Antimicrobial Activity of *Elfvingia applanata* Extract Alone and in Combination with Narigenin," The Korean Journal of Mycology, vol. 23, No. 2, pp. 153-160 Mar. 1995.

Young So Kim, "Antimicrobial Activity of *Elfvingia applanata* extract alone and in Combination with Some Antibiotics," Yakhak Hoeji, vol. 38, No. 6 pp. 742-748 1994.

*Primary Examiner*—Christopher R Tate
*Assistant Examiner*—Randall Winston
(74) *Attorney, Agent, or Firm*—Kirk Hahn

(57) ABSTRACT

The present invention relates to a non-polar solvent soluble extract, polyphenol fractions therefrom and the compounds isolated from *Elfvingia applanata*, which shows a therapeutic activity for diabetes and diabetic complications, and a pharmaceutical composition for the treatment of diabetes and diabetic complications comprising the same.

7 Claims, No Drawings

PHARMACEUTICAL COMPOSITION COMPRISING AN EXTRACT OR COMPOUNDS ISOLATED FROM *ELFVINGIA APPLANATA* FOR THE PREVENTION AND THE TREATMENT OF DIABETES AND DIABETIC COMPLICATIONS

This application is the U.S. National Phase under 35 U.S.C. §371 of International Application PCT/KR03/411, filed on Mar. 3, 2003, which claims priority of Korean Patent Application No. 10-2003-0005776 filed on Jan. 29, 2003 and Korean Patent Application No. 10-2003-0005778 filed on Jan. 29, 2003. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention relates to a pharmaceutical composition comprising a non-polar solvent soluble extract, polyphenol fractions therefrom or the compounds isolated from *Elfvingia applanata* for the prevention and the treatment of diabetes and diabetic complications.

BACKGROUND OF ART

Diabetes mellitus is a mammalian condition in which the amount of glucose in the blood plasma is abnormally high. Elevated glucose levels in some instances can lead to higher than normal amounts of particular hemoglobin, HbA1c. This condition can be life-threatening and high glucose levels in the blood plasma, hyperglycemia, can lead to a number of chronic diabetes syndromes, for example, atherosclerosis, microangiopathy, kidney disorders or failure, cardiac disease, diabetic retinopathy and other ocular disorders, including blindness.

Diabetes mellitus is known to be existed in two forms of the disease. One of those is known as Type II, non-insulin dependent diabetes (NIDDM) or adult-onset, and another is juvenile diabetes or Type I, of which pancreas often continues to secrete normal amounts of insulin. However, this insulin is ineffective in preventing the symptoms of diabetes which include cardiovascular risk factors such as hyperglycemia, impaired carbohydrate mechanism, particularly glucose metabolism, glycosuria, decreased insulin sensitivity, centralized obesity hypertriglyceridemia, low HDL levels, elevated blood pressure and various cardiovascular effects. Many of these cardiovascular risk factors are known to precede the onset of diabetes by as much as a decade. These symptoms, if left untreated, often lead to severe complications, including premature atherosclerosis, retinopathy, nephropathy, and neuropathy. Insulin resistance is believed to be a precursor to overt NIDDM and strategies directed toward ameliorating insulin resistance may provide unique benefits to patients with NIDDM.

Current drugs used for managing Type II diabetes and its precursor syndromes, such as insulin resistance, fall within five classes of compounds: the biguanides, thiazolidinediones, the sulfonylureas, benzoic acid derivatives and alpha-glucosidase inhibitors. The biguanides, such as metformin, are believed to prevent excessive hepatic gluconeogenesis. The thiazolidinediones are believed to act by increasing the rate of peripheral glucose disposal. The sulfonylureas, such as tolbutamide and glyburide, the benzoic acid derivatives, such as repaglinide, and the alpha-glucosidase inhibitors, such as acarbose, lower plasma glucose primarily by stimulating insulin secretion.

Above sulfonylureas have disadvantages that these drugs cannot be administered to IDDM patient, NIDDM patient having decreased insulin secretion, and fecund female being worried about anomalous child birth, abortion and stillbirth. Additionally, most of the sulfonylureas should be administered carefully to liver dysfunction patient and kidney dysfunction patient because of sulfonylurea metabolism.

The pathway of biguanides such as metformin has not been verified clearly but the biguanides cannot increase the insulin secretion of pancreas. The biguanides have lower glucose-decreasing effect than the sulfonylureas but have low occurrence of hypoglycemia. And the biguanides treatment may happen nausea, vomiting, diarrhea, eruption etc. in early stage and causes lactic acidosis of fatal side effect, so those are used only as experimental agents in U.S.A.

The sulfonylureas or the biguanides have above disadvantages and side effects; therefore it is required to develop a new hypoglycemic drug having fewer side effects and greater safeties for effective treatment than those of current drugs.

*Elfvingia applanata* KARST employed in the present invention belong to Polyporaceae and is distributed all over the world. *Elfvingia applanata* KARST, white rot mycelium, grows naturally on a latifoliate tree horizontally in summer and its fruit body is an annual plant in the form of semicircle and is known to have anti-cancer effect.

DISCLOSURE OF THE INVENTION

Accordingly, it is an object of the present invention to provide a non-polar solvent soluble extract, polyphenol fractions therefrom, and the compounds isolated from *Elfvingia applanata*, which have an inhibitory activity of aldose reductase.

It is another object of the present invention to provide a process for preparing the extract and fractions to treat diabetes and diabetic complications.

It is another object of the present invention to provide a pharmaceutical composition comprising the extract or fractions, optionally in combination with a pharmaceutically acceptable carrier, additive or excipient, for the prevention and treatment of diabetes and diabetic complications without creating side effects.

It is another object of the present invention to provide a pharmaceutical composition comprising of phenyl derivatives of the following general formula (I) isolated from *Elfvingia applanata* and a pharmaceutically acceptable salt thereof, optionally in combination with a pharmaceutically acceptable carrier, additive or excipient, for the prevention and treatment of diabetes and diabetic complications without creating side effects:

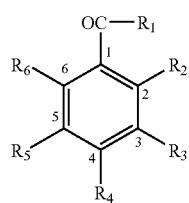

(I)

Wherein, $R_1$ is hydrogen atom, hydroxy group, alkyl or alkoxy group of 1 to 4 carbon atoms;

$R_2$ to $R_6$ are independently selected from hydrogen atom, hydroxy group, alkyl or alkoxy group of 1 to 4 carbon atoms.

Preferable compounds are 2,5-dihydroxy benzoic acid of the following chemical formula (II) and protocatechualdehyde of the following chemical formula (III) respectively.

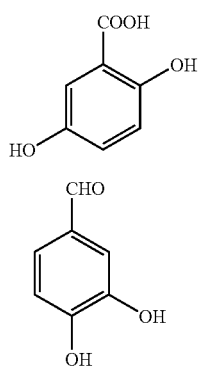

(II)

(III)

The pharmaceutically acceptable salt of the compound of the present invention comprises the acid addition salt and base addition salt thereof. Examples of the salt are salts of hydroxy group such as sodium, calcium, and potassium salt of hydroxy group; and salts of amine groups such as hydrobromide, sulfate, hydrogen sulfate, phosphate, hydrogen phosphate, dihydrogen phosphate, acetate, succinate, citrate, tartrate, lactate, mandelate, methane sulfonate(methylate), and p-toluene sulfonate(tosylate), which may be prepared in accordance with any of the conventional procedures.

It is another object of the present invention to provide a pharmaceutical composition comprising at least one compound selected from the group consisting of:

cerebroside of the following general formula (IV);

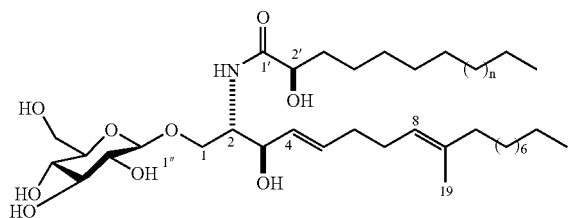

(IV)

wherein, n=7 to 9, 5-dihydroergosterol of the following chemical formula (V);

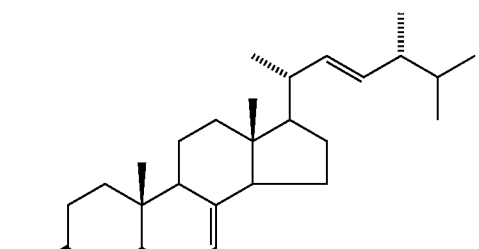

(V)

2-methoxyfatty acid of the following general formula (VI); and

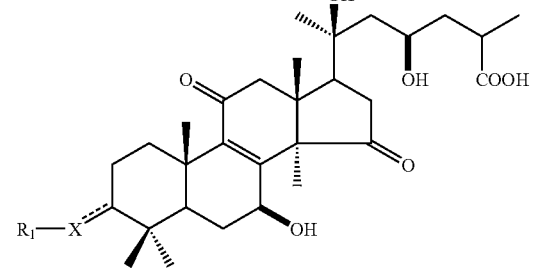

(VI)

wherein, n=12 to 15, cerevisterol of the following chemical formula (VII).

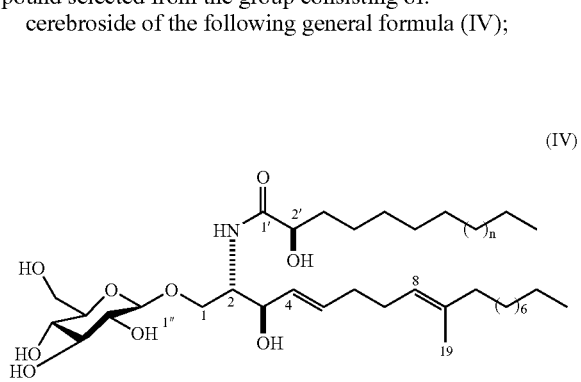

(VII)

isolated from *Elfvingia applanata*, optionally in combination with a pharmaceutically acceptable carrier, additive or excipient, for the prevention and treatment of diabetes and diabetic complications.

It is another object of the present invention to provide applanatic acid derivatives having novel structure of the following general formula (VIII) isolated from *Elfvingia applanata*, and a pharmaceutically acceptable salt and isomer thereof:

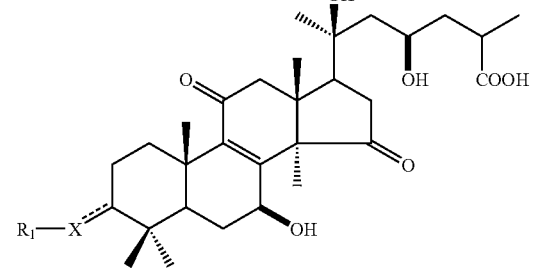

(VIII)

Wherein,

X is an oxygen, sulfur or nitrogen atom;

$R_1$ is a hydrogen or an alkyl group of 1 to 4 carbon atoms; and

----- is a single bond or double bond.

Preferable compounds are applanatic acid C of the following chemical formula (IX) and applanatic acid D of the following chemical formula (X):

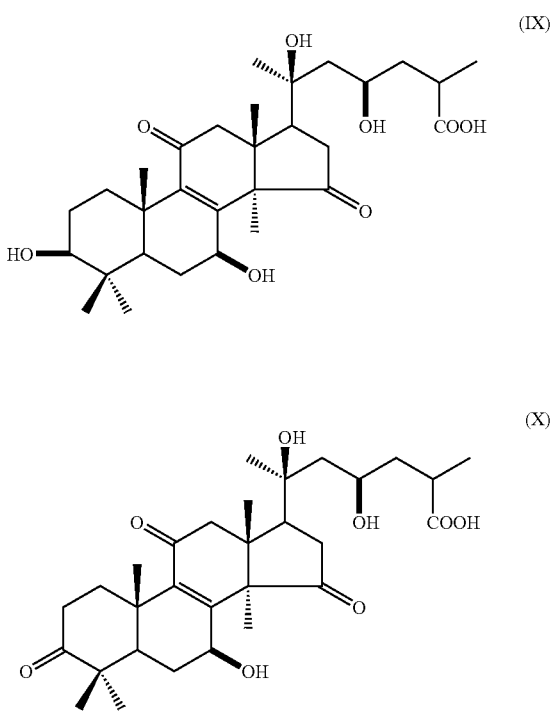

The compound of the present invention contains one or plural asymmetric carbon atoms, and thus gives rise to optical isomers such as (R)- and (S)-isomers, racemates, diastereoisomers, etc.

Accordingly, the present invention includes all such possible isomers, and their racemic and resolved, enantiomerically pure forms, as well as all mixtures thereof. Further, the invention includes the use of said compounds and the process of preparation and isolation thereof known to those skilled in the art.

The pharmaceutically acceptable salt of the compound of the present invention comprises the acid addition salt and base addition salt thereof. Examples of the salt are salts of hydroxy group such as sodium, calcium, and potassium salt of hydroxy group; and salts of amine groups such as hydrobromide, sulfate, hydrogen sulfate, phosphate, hydrogen phosphate, dihydrogen phosphate, acetate, succinate, citrate, tartrate, lactate, mandelate, methane sulfonate(methylate), and p-toluene sulfonate(tosylate), which may be prepared in accordance with any of the conventional procedures.

The compound may be in form of enantiomer due to a chiral center. Accordingly the compound of the present invention may include all of optical isomer and stereoisomer, and the mixture thereof. The present invention comprises the racemic mixture, at least one enantiomer and diastereomer; the use of the mixture thereof; and the process of preparation and isolation thereof known to those skilled in the art.

It is another object of the present invention to provide a pharmaceutical composition comprising the compound of the present invention, and a pharmaceutically acceptable salt and isomer thereof, optionally in combination with a pharmaceutically acceptable carrier, additive or excipient, for the prevention and treatment of diabetes and diabetic complications without creating side effects.

It is another object of the present invention to provide a use of the compound of the present invention for the preparation of pharmaceutical composition to treat diabetes and diabetic complications.

It is another object of the present invention to provide a method for treatment of diabetes and diabetic complications comprising administering a therapeutically effective amount of the composition comprising said extract, said fraction or isolated compound of the present invention.

The diabetic complication includes hyperglycemia, atherosclerosis, microangiopathy, kidney disorders and failure, cardiac disease, diabetic retinopathy and other ocular disorders.

In accordance with on aspect of the present invention, there are provided the extract, polyphenol fractions therefrom and the compounds isolated from *Elfvingia applanata*, which shows an effective therapeutic activity against diabetes and diabetic complications by inhibiting aldose reductase; and a pharmaceutical composition for the treatment of diabetes and diabetic complications, which comprises the same, optionally in combination with a pharmaceutically acceptable carrier, additive or excipient.

In accordance with the present invention, it has been found that the extract, the fractions and the compounds isolated from *Elfvingia applanata* possesses the ability to prevent diabetes complications by inhibiting activity of aldose reductase.

The extract, the fractions and the compounds of the present invention may be prepared in accordance with the following preferred embodiment:

Dried *Elfvingia applanata* is pulverized and mixed with 1 to 10-fold, preferably, 5 to 15-fold volume of polar solvent such as water, lower alcohols having 1 to 4 carbon atoms, or a 1:0.1 to 1:10, preferably 1:0.2 to 1:3 mixtures thereof. The resulting mixture is subjected to extraction such as reflux-extraction, ultrasonification extraction method and the like, to obtain a crude extract, wherein the extraction is carried out at a temperature ranging from 20 to 100° C., preferably 40 to 60° C., for a period ranging from 0.5 hours to 2 days, preferably 2 hours to 24 hours, with 1 to 5 times, preferably 2 to 5 times. The crude extract is dispersed in polar solvent e.g. water, methanol, etc., and further extracted 1 to 10 times, preferably 2 to 5 times using 1 to 100-fold, preferably, 1 to 5-fold volume of non-polar solvent e.g. hexane, chloroform, dichloromethane, ethylacetate, etc., to obtain the non-polar solvent soluble extract. The resulting non-polar solvent soluble extract is subjected to silica gel column chromatography, liquid chromatography (LC) and thin layer chromatography (TLC) successively to isolate purposed compounds.

Hereinafter, the process for preparing the extract, the fractions, and the compounds of the present invention is described in detail.

The non-polar solvent soluble extract of the present invention may be prepared by the process comprising the steps of:

1) Pulverizing of a dried *Elfvingia applanata;*

2) Subjecting the powder to reflux-extraction with a polar solvent;

3) Filtering and evaporating the resultant in vacuum to obtain a crude extract;

4) Dispersing the crude extract in water;

5) Separating the solution with non-polar solvent such as hexane, ethylacetate and methylene chloride in a separating funnel, to obtain non-polar solvent soluble layer and water soluble layer; and 6) Filtering and evaporating the non-polar solvent layer in vacuum to obtain a non-polar solvent soluble extract.

Alternatively, a polar solvent soluble extract may be prepared by further extracting the water soluble layer in the step (5) with the polar solvent, and filtering and evaporating the polar solvent layer in vacuum.

The polyphenol fractions of the present invention may be prepared by the process comprising the steps of:

Subjecting the non-polar solvent soluble extract obtained from the step (6) to silica gel column chromatography using a solvent mixture of hexane:ethylacetate:methanol with a ratio of 1:1:1 to 50:10:0.5 (W/W), preferably 10:3:1 as an eluent, to obtain the polyphenol fraction A and B, respectively obtained from 8th and 9th fraction among 15 fractions; or Subjecting the extract obtained from the step (6) to reverse phase chromatography with Sephadex LH-20, wherein the column is eluted with linear gradient using a solvent mixture of methanol:water, to obtain the polyphenol fraction C and D, respectively obtained from 2nd and 4th fraction among 4 fractions.

The phenyl derivatives of the present invention may be prepared by the process comprising the steps of:

1) Subjecting the ethylacetate soluble extract of the step (6) to silica gel column chromatography using as an eluent, a solvent mixture of hexane:ethylacetate:methanol with a ratio of 1:1:1 to 50:10:0.5 (W/W), preferably 10:3:1 to obtain 15 fractions; and 2) Subjecting the 6th and the 7th fraction among above 15 fractions to silica gel column chromatography using the a solvent mixture of toluene:ethylacetate:acetic acid with a ratio of 50:10:0.5 to 0.5:10:50 (w/w), preferably 5:3:1 to 2.5:1:0.5 as an eluent, to obtain the phenyl derivatives, 2,5-dihydroxy benzoic acid having $R_f$ value of 0.58 and protocatechualdehyde having $R_f$ value of 0.52 on TLC (eluent:toluene:ethyl acetate:acetic acid=5:4:1) respectively.

The cerebroside compound of the present invention may be prepared by the process comprising the steps of:

1) Subjecting the polar solvent soluble extract to silica gel column chromatography using as an eluent, a solvent mixture of hexane:ethylacetate:methanol with a ratio 1:1:1 to 50:10:0.5 (W/W), preferably 10:3:1, to obtain 15 fractions; and 2) Subjecting the 3rd fraction among above 15 fractions to further silica gel column chromatography (1.5×10 cm, Merck, ASTM 7729, German) using a solvent mixture of chloroform:methanol:water with a ratio of 50:10:0.5 to 0.5:10:50 (w/w), preferably 7:1:0.5 as a eluent, to obtain cerebroside having $R_f$ value of 0.51 on TLC (eluent:chloroform:methanol:water=7:2:0.5).

The 2-methoxyfatty acid, 5-dihydroergosterol and cerevisterol compound of the present invention may be prepared by the process comprising the steps of:

1) Subjecting the non-polar solvent soluble extract of the step (6) to silica gel column chromatography, wherein the column is eluted with linear gradient using a 1 to 100% of chloroform-methanol solvent, to obtain 16 fractions; and 2) Subjecting the 6th fraction and 9th fraction among above 16 fractions to recrystallization to obtain 2-methoxyfatty acid having $R_f$ value of 0.91 and 5-dihydroergosterol having $R_f$ value of 0.76 on TLC (eluent:hexane:ethylacetate=1:10) respectively; or Subjecting the 12th fraction among above 16 fractions to silica gel column chromatography (1.5×10 cm, merck, ASTM 7729, German) using a solvent mixture of hexane:ethylacetate with a ratio of 10:1, 8:5, 5:8 or 1:10 (w/w) as a eluent, to obtain cerevisterol having $R_f$ value of 0.16 on TLC (eluent:hexane:ethylacetate=1:10).

The applanatic acid derivatives of the present invention may be prepared by the process comprising the steps of:

1) Subjecting the non-polar solvent soluble extract of the step (6) to silica gel column chromatography using a solvent mixture of chloroform:methanol with a ratio of 1:100 to 100:1(W/W) as an eluent, to obtain 16 fractions; and Subjecting the 11th and 10th fraction among above 16 fractions to further silica gel column chromatography using a solvent mixture of hexane:ethylacetate with a ratio of 10:1 to 1:10, preferably 8:5 to 5:8 as an eluent, to obtain applanatic acid derivatives, applanatic acid C having $R_f$ value of 0.58 and applanatic acid D having $R_f$ value of 0.52 on TLC (eluent:hexane:ethyl acetate=2:1) respectively.

The extract, the fractions, and the compounds of the present invention exhibits a high level of ability to inhibit activity of aldose reluctase which may cause diabetic complications such as neuropathy, retinopathy, cataract, nephropathy and the like.

As described above, the extract, the fractions, and the compounds of *Elfvingia applanata* KARST can be used as an effective pharmaceutical composition for the treatment of diabetes, which has little toxicity and causes no adverse effect.

Accordingly, the present invention also provides a pharmaceutical composition for treatment of diabetes, which comprises the extract, the fractions or the compounds isolated from *Elfvingia applanata* KARST as an active ingredient, optionally in combination with pharmaceutically acceptable excipients, carriers or diluents.

The pharmaceutical formulation may be prepared by using the composition in accordance with any of the conventional procedures. In preparing the formulation, the active ingredient is preferably admixed or diluted with a carrier or enclosed within a carrier, which may be in the form of a capsule, sachet or other container. When the carrier serves as a diluent, it may be a solid, semi-solid or liquid material acting as a vehicle, excipient or medium for the active ingredient. Thus, the formulations may be in the form of a tablet, pill, powder, sachet, elixir, suspension, emulsion, solution, syrup, aerosol, soft and hard gelatin capsule, sterile injectable solution, sterile packaged powder and the like.

Examples of suitable carriers, excipients, and diluents are lactose, dextrose, sucrose, mannitol, starches, gum acacia, alginates, gelatin, calcium phosphate, calcium silicate, cellulose, methylcellulose, microcrystalline cellulose, polyvinylpyrrolidone, water, methylhydroxybenzoates, propylhydroxybenzoates, talc, magnesium stearate and mineral oil.

The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

The pharmaceutical formulations can be administered via various routes including oral, transdermal, subcutaneous, intravenous and intramuscular introduction. A typical daily dose of the active ingredient may range from about 0.01 to 500 mg/kg body weight, preferably 0.1 to 100 mg/kg body weight, and can be administered in a single dose or in divided dose. However, it should be understood that the amount of the active ingredient actually administered ought to be determined in light of various relevant factors including the condition to be treated, the chosen route of administration, the age, sex and body weight of the individual patient, and the severity of the patient's symptom; and. Therefore, the above dose should not be intended to further illustrate the present invention without limiting its scope.

BEST MODE FOR CARRYING OUT THE INVENTION

The following Examples and Experimental Examples are intended to further illustrate the present invention without limiting its scope.

EXAMPLE 1

Preparation of the Crude Extract of *Elfvingia applanata*

2.1 kg of dried *Elfvingia applanata* (collected in Ontario, Canada) was pulverized. Powdered *Elfvingia applanata* was subjected to reflux-extraction with 5 l of methanol for 1 hr at 50° C., 5 times and collected each extracts. The extract was filtered with the filter paper (Whatman, USA) and evaporated in vacuum using evaporator (Eyela, N-N series, Japan) at below 50° C., to afford 85 g of crude extract of *Elfvingia applanata*.

EXAMPLE 2

Preparation of Polar and Non-polar Solvent Soluble Extract of *Elfvingia applanata*

The crude extract of the example 1 was dispersed in 1.5 l of water and mixed with 1.5 l of hexane. The mixture was partitioned into the hexane-insoluble layer (lower layer) and the hexane-soluble layer (upper layer) in a separating funnel, and then the hexane-soluble layer was collected. The remaining hexane-insoluble layer (lower layer) was extracted repeatedly until the color of the solution get pale. The resulting hexane-soluble extract was filtered and concentrated under reduced pressure. According to the similar procedures to above described procedure except altering the solvent system, hexane soluble extract (15 g), methylene chloride soluble extract (25 g), ethylacetate soluble extract (30 g) and butanol soluble extract (15 g) were prepared to use as a samples in following Experimental Example.

EXAMPLE 3

Preparation of the Polyphenol Fraction 30 g of the ethylacetate soluble extract of the Example 2 was subjected to silica gel column chromatography (12×60 cm, Merck, ASTM 7734, German) using as an eluent, a solvent mixture of hexane:ethylacetate:methanol with a ratio of 10:3:1, to obtain 15 fractions. Among above 15 fractions, 1.5 g of 8th fraction and 2.5 g of 9th fraction were designated as polyphenol fraction A and B respectively. Alternatively, 2.5 g of ethylacetate-soluble extract was subjected to Sephadex LH-20 column chromatography (2.5×60 cm, Pharmacia, Sweden) using as an eluent, a solvent mixture of methanol:water with a ratio of 3:7 to 10:0 obtain 4 fractions. Among above fractions, 0.3 g of 2nd fraction and 0.2 g of 4th fraction were designated as polyphenol fraction C and D respectively.

EXAMPLE 4

Isolation of 2,5-dihydroxybenzoic acid from *Elfvingia applanata*

30 g of the ethylacetate soluble extract of the Example 2 was subjected to silica gel column chromatography (12×60 cm, Merck, ASTM 7734, German) using as an eluent, a solvent mixture of hexane:ethylacetate:methanol with a ratio of 10:3:1, to obtain 15 fractions. Among above 15 fractions, 6th fraction was subjected to silica gel column chromatography (1.5×15 cm, Merck, ASTM 7729, German) using as an eluent, a solvent mixture of toluen:ethylacetate:acetic acid with a ratio of 5:3:1 and further to TLC using a solvent mixture of toluene:ethylacetate:acetic acid with a ratio of 5:4:1 to obtain 7 mg of dihydroxybenzoic acid having $R_f$ value of 0.58. 2,5-dihydroxy benzoic acid was identified by EI-Mass and $^1$H-NMR spectra and was used as a sample in following Experimental Example.

Melting point; 189-194° C. $^1$H-NMR (300 MHz, $CD_3OD$): 6.76 (1H, d, J=9.0 Hz, H-3), 6.95 (1H, dd, J=3.0, 8.7 Hz, H-4), 7.24 (1H, d, J=3.0 Hz, H-6), EI-MS m/z (rel. int., %): 154 $[M]^+$ (12.9), 136 $[M-H_2O]^+$ (100), 108 $[M-(COOH+H)]^+$ (51.6), 80 (66.1).

EXAMPLE 5

Isolation of Protocatechualdehyde from *Elfvingia applanata*

30 g of the ethylacetate soluble extract of the Example 2 was subjected to silica gel column chromatography (12×60 cm, Merck, ASTM 7734, German) using as an eluent, a solvent mixture of hexane:ethylacetate:methanol with a ratio of 10:3:1, to obtain 15 fractions. Among above 15 fractions, 7th fraction was subjected to silica gel column chromatography (1.5×15 cm, Merck, ASTM 7729, German) using a solvent mixture of toluen:ethylacetate:acetic acid with a ratio of 2.5:1:0.5 and further to TLC using as an eluent, a solvent mixture of toluene:ethylacetate:acetic acid with a ratio of 5:4:1, to obtain 2 mg of protocatechualdehyde having $R_f$ value of 0.52. protocatechualdehyde was identified by EI-Mass and $^1$H-NMR spectra and was used as a sample in following Experimental Example.

Melting point: 144-151° C. $^1$H-NMR (300 MHz, $CD_3OD$): 6.90 (1H, d, J=8.1 Hz, H-5), 7.29 (1H, d, J=2.1 Hz, H-2), 7.30 (1H, dd, J=2.1, 9.0 Hz, H-6), 9.68 (1H, s, CHO), EI-MS m/z (rel. int., %):138 $[M]^+$ (100), 137 $[M-H]^+$ (59.0), 110 $[M-CO]^+$ (31.1), 109 $[M-CHO]^+$ (24.6), 97 (13.1), 81 (22.1).

EXAMPLE 6

Isolation of Cerebroside from *Elfvingia applanata*

30 g of the ethylacetate soluble extract of the Example 2 was subjected to silica gel column chromatography (12×60 cm, Merck, ASTM 7734, German) using as an eluent, a solvent mixture of hexane:ethylacetate:methanol with a ratio of 10:3:1, to obtain 15 fractions. Among above 15 fractions, 3rd fraction was subjected to silica gel column chromatography (1.5×10 cm, Merck, ASTM 7729, German) using as an eluent, a solvent mixture of chloroform:methanol:water with a ratio of 7:1:0.5 and further to TLC using as an eluent, a solvent mixture of chloroform:methanol:water with a ratio of 7:2:0.5, to obtain 5 mg of cerebroside having $R_f$ value of 0.51. Cerebroside of the following general formula (IV) was identified by $^1$H-NMR, $^{13}$C-NMR and (+)-FA BMS and was used as a sample in following Experimental Example:

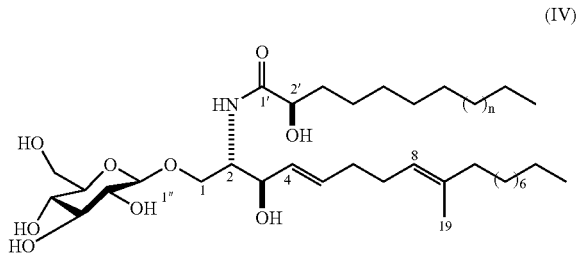

(IV)

wherein, n=7 to 9.

n=7, [(2S,3R,4E,8E)-1-O-β-D-glucopyranosyl-3-hydroxy-2-[(R)-2'-hydroxypalmitoyl]amino-9-methyl-4,8-octadecadiene, n=8, (2S,3R,4E,8E)-1-O-β-D-glucopyranosyl-3-hydroxy-2-[(R)-2'-hydroxy heptadecanoyl]amino-9-methyl-4,8-octadecadiene, n=9, (2S,3R,4E,8E)-1-O-β-D-glucopyranosyl-3-hydroxy-2-[(R)-2'-hydroxy stearoyl]amino-9-methyl-4,8-octadecadiene.

Melting point: 155-164° C. $^1$H-NMR (300 MHz, pyridine-$d_5$) d: 0.85 (3H, t, J=6.9 Hz, $CH_3$), 1.25, 1.27 [($CH_2$)n], 1.60 (3H, br s, 9-$CH_3$), 2.00 (2H, m, H-10), 2.14 (4H, m, H-6, 7), 3.88 (1H, m, H-5"), 4.01 (1H, dd, J=7.5, 9.0 Hz, H-2"), 4.19 (1H, t, J=8.7 Hz, H-3"), 4.22 (1H, dd, J=3.6, 11.4 Hz, H-1a), 4.33 (1H, dd, J=5.4, 11.7 Hz, H-6"a), 4.49 (1H, dd, J=2.4, 11.7 Hz, H-6"b), 4.56 (1H, dd, J=3.6, 7.2 Hz, H-2'), 4.69 (1H, dd, J=5.7, 10.2 Hz, H-1b), 4.77 (1H, m, H-3), 4.81 (1H, m, H-2), 4.90 (1H, d, J=7.8 Hz, H-1"), 5.24 (1H, t-like, J=5.7 Hz, H-8), 5.92 (1H, dt, J=5.7, 15.3 Hz, H-5), 6.00 (1H, dd, J=5.4, 15.3 Hz, H-4), 8.33 (1H, d, J=8.4 Hz, NH); $^{13}$C-NMR (75.5 MHz, pyridine-$d_5$) d: 14.3 (18-$CH_3$), 16.1 (19-$CH_3$), 22.9 (C-17), 25.9 (C-4'), 28.2 (C-11), 28.3 (C-7), 29.5, 29.6, 29.9, 30.0, 32.1, 33.0 (C-6), 35.6 (C-3'), 40.0 (C-10), 54.6 (C-2), 62.6 (C-6"), 70.1 (C-1), 71.5 (C-4"), 72.3 (C-2'), 72.5 (C-3), 75.1 (C-2"), 78.4 (C-3"), 78.5 (C-5"), 105.6 (C-1"), 124.1 (C-8), 131.9 (C-5), 132.3 (C-4), 135.8 (C-9), 175.6 (C-1'); (+)-FA BMS m/z 750 [(M+Na)$^+$, $C_{41}H_{77}O_9N$], 764 [(M+Na)$^+$, $C_{42}H_{79}O_9N$], 778 [(M+Na)$^+$, $C_{43}H_{81}O_9N$], 562 (M−179).

EXAMPLE 7

Isolation of 5-dihydroergosterol from *Elfvingia applanata*

25 g of the methylene chloride soluble extract of the Example 2 was subjected to silica gel column chromatography (10×45 cm, Merck, ASTM 7729, German). The column was eluted with linear gradient using 1, 2, 3, 5, 10, 50 and 100% of chloroform-methanol solvent to obtained 16 fractions. Among above 16 fractions, 9th fraction was subjected to recrystallization to obtain 25 mg of 5-dihydroergosterol having $R_f$ value of 0.76 on TLC using as an eluent, a solvent mixture of hexane:ethylacetate with a ratio of 1:10. 5-dihydroergosterol was identified by $^1$H-NMR and $^{13}$C-NMR spectra and was used as a sample in following Experimental Example.

Melting point: 170-173° C. $^1$H-NMR (300 MHz, $CDCl_3$) δ: 0.54 (3H, s, 18-$CH_3$), 0.80 (3H, s, 19-$CH_3$), 0.82 (3H, d, J=6.9 Hz, 26-$CH_3$), 0.84 (3H, d, J=6.6 Hz, 27-$CH_3$), 0.91 (3H, d, J=6.9 Hz, 28-$CH_3$), 1.02 (3H, d, J=6.9 Hz, 21-$CH_3$), 3.60 (1H, m, H-3), 5.19 (2H, m, H-22,23); $^{13}$C-NMR (75.5 MHz, $CDCl_3$) δ: 37.1 (C-1), 31.5 (C-2), 71.1 (C-3), 38.0 (C-4), 40.3 (C-5), 29.6 (C-6), 117.5 (C-7), 139.5 (C-8), 49.5 (C-9), 34.2 (C-10), 21.5 (C-11), 39.5 (C-12), 43.3 (C-13), 43.3 (C-14), 55.1 (C-15), 22.9 (C-16), 56.0 (C-17), 12.1 (C-18), 13.0 (C-19), 40.5 (C-20), 21.1 (C-21), 135.7 (C-22), 131.9 (C-23), 42.8 (C-24), 33.1 (C-25), 19.9 (C-26), 19.6 (C-27), 17.6 (C-28); EI-MS m/z (rel. int., %) 398 [M]$^+$ (16.5), 383 [M−$CH_3$]$^+$ (7.4), 355 [M−$C_3H_7$]$^+$ (2.5) 300 (8.3), 285 [300-$CH_3$]$^+$ (3.3), 273 [M−SC($C_9H_{17}$)]$^+$ (17.4), 271 [M−(SC+2H)]$^+$ (54.5), 255 [M−(SC+$H_2O$)]$^+$ (18.2), 229 (9.9), 213 [M−(ring D+$H_2O$)]$^+$ (7.4), 55 (100).

EXAMPLE 8

Isolation of 2-methoxyfatty Acid from *Elfvingia applanata*

25 g of the methylene chloride soluble extract of the Example 2 was subjected to silica gel column chromatography (10×45 cm, Merck, ASTM 7729, German). The column was eluted with linear gradient using 1, 2, 3, 5, 10, 50 and 100% of chloroform-methanol solvent to obtained 16 fractions. Among above 16 fractions, 6th fraction was subjected to recrystallization to obtain 18 mg of 2-methoxy fatty acid having $R_f$ value of 0.91 on TLC using as an eluent, a solvent mixture of hexane:ethylacetate with a ratio of 1:10. 2-methoxy fatty acid of the following general formula (VI) was identified by EI-Mass, $^1$H-NMR and $^{13}$C-NMR spectra and was used as a sample in following Experimental Example:

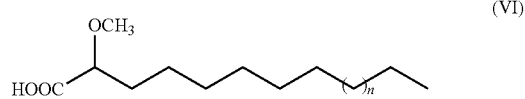

(VI)

wherein, n=12 to 15.

Melting point: 64-65° C. $^1$H-NMR (300 MHz, pyridine-$d_5$) δ: 0.86 (3H, d, J=6.6 Hz, $CH_3$), 1.25, 1.30 [each s, ($CH_2$)$_n$], 3.71 (3H, s, 2-$OCH_3$), 4.55 (1H, dd, J=5.1, 7.4 Hz, H-2); $^{13}$C-NMR (75.5 MHz, pyridine-$d_5$) δ: 175.9 (C-1), 71.2 (C-2), 51.5 ($OCH_3$), 35.2, 32.1, 30.0, 29.9, 29.7, 29.6, 25.7, 22.9, 14.3 ($CH_3$); EI-MS m/z (rel. int., %) 412 [M]$^+$ (2-methoxypentacosanoic acid, 0.8), 398 [M]$^+$ (2-methoxylignoceric acid, 5.8), 384 [M]$^+$ (2-methoxytricosanoic acid, 1.5), 370 [M]$^+$ (2-methoxybenzoic acid, 2.1), 90 [$C_3H_6O_3$]$^+$ (23.1).

EXAMPLE 9

Isolation of Cerevistrol from *Elfvingia applanata*

25 g of the methylene chloride soluble extract obtained of the Example 2 was subjected to silica gel column chromatography (10×45 cm, Merck, ASTM 7729, German). The column was eluted with linear gradient using 1, 2, 3, 5, 10, 50 and 100% of chloroform-methanol solvent mixture to obtained 16 fractions. Among above 16 fractions, 12th fraction was subjected to silica gel column chromatography (1.5×10 cm, Merck, ASTM 7729, German) using as an eluent, a solvent mixture of hexane:ethylacetate with a ratio of 10:1, 8:5, 5:8 and 1:10, to obtain 7 mg of cerevistrol having $R_f$ value of 0.16 on TLC using as an eluent, a solvent mixture of hexane:ethylacetate with a ratio of 1:10. cerevistrol was identified by EI-Mass, $^1$H-NMR and $^{13}$C-NMR spectra and was used as a sample in following Experimental Example.

Melting point: 224-226° C. $^1$H-NMR (300 MHz, pyridine-$d_5$) δ: 0.65 (3H, s, 18-$CH_3$), 0.84 (3H, d, J=6.6 Hz, 26-$CH_3$), 0.85 (3H, d, J=6.9 Hz, 27-$CH_3$), 0.94 (3H, d, J=6.9 Hz, 28-$CH_3$), 1.05 (3H, d, J=6.3 Hz, 21-$CH_3$), 1.54 (3H, s, 19-$CH_3$), 4.33 (1H, br s, H-6), 4.84 (1H, m, H-3), 5.16 (1H, dd, J=7.8, 15.3 Hz, H-22), 5.24 (1H, d, J=6.9, 15.3 Hz, H-23), 5.74 (1H, t, J=2.4 Hz, H-7); EI-MS m/z (rel. int., %) 412 [M–$H_2O$]$^+$ (20.5), 397 [M–$H_2O$–$CH_3$]$^+$ (6.6), 394 [M–$2H_2O$]$^+$ (10.6), 382 [M–$H_2O$-$2CH_3$]$^+$ (11.5), 379 [M–$2H_2O$–$CH_3$]$^+$ (18.0), 376 [M–$3H_2O$]$^+$ (3.3), 369 [M–$H_2O$–$C_3H_7$]$^+$ (2.5), 287 [M–$H_2O$—SC($C_9H_{17}$)]$^+$ (2.5), 269 [M-(SC+$2H_2O$)]$^+$ (14.8), 251 [M-(SC+$3H_2O$)]$^+$ (27.9), 107 (29.5), 105 (59.5), 81 (43.4), 69 (100), 55 (94.3).

EXAMPLE 10

Isolation of Applanatic Acid C from *Elfvingia applanata*

25 g of the methylene chloride soluble extract of the Example 2 was subjected to silica gel column chromatography (10×45 cm, Merck, ASTM 7734, German). The column was eluted with linear gradient using 1, 2, 3, 5, 10, 50 and 100% of chloroform-methanol solvent mixture to obtained 16 fractions. Among the 16 fractions, 11th fraction was subjected to silica gel column chromatography (2×8 cm, Merck, ASTM 7734, German) using as an eluent, a solvent mixture of hexane:ethylacetate with a ratio of 10:1, 8:5, 5:8 and 1:10, to obtain 70 mg of applanatic acid C having $R_f$ value of 0.32 on TLC using as an eluent, a solvent mixture of hexane:ethylacetate with a ratio of 1:10. Applanatic acid C, (20S,23R)-3β,7β,20,23-tetrahydroxy-11,15-dioxolanosta-8-en-26-oic acid of the following chemical formula (IX) was identified by UV, IR, EI-Mass and NMR spectra (See Table 1) and was used as a sample in following Experimental Example:

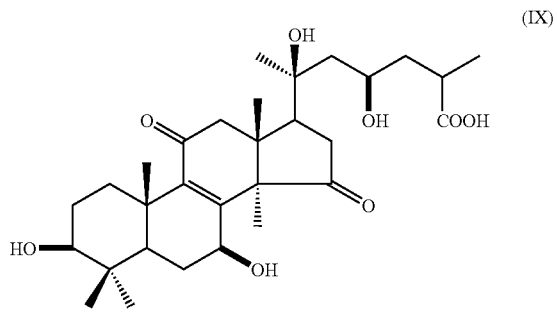

(IX)

Melting point: 227-230° C. $[α]_D^{26}$=+117.5 (c=0.211, CHCl$_3$), UV λ$_{max}$ (methanol) 252 nm (log ε 4.34), IR γ$_{max}$ 3430 (OH), 1773 (five-membered ring C=O), 1711 (COOH), 1647 (α,β-unsaturated C=O), 1458 ($CH_2$), 1377 ($CH_3$), 1181, 1034 (OH), 926 cm$^{-1}$, EI-MS m/z (rel. int., %): 516 [M–$H_2O$]+ (2.5), 498 [M–$2H_2O$]+ (0.8), 470 [M-($2H_2O$+CO)]$^+$ (5.8), 358 [M-side chain (SC)—H]$^+$ (1.7), 313 [M–SC—(CO+$H_2O$)]$^+$ (0.8), 175 [$C_8H_{15}O_4$, side chain (SC)]$^+$ (8.3), 157 [SC—$H_2O$]$^+$ (8.3), 99 (45.5), 69 (100), 55 (100), (+)—HR FAB MS m/z 539.2982, calculation value [$C_{30}H_{44}O_7$Na (M+Na—$H_2O$)$^+$: 539.2985]

EXAMPLE 11

Isolation of Applanatic Acid D from *Elfvingia applanata*

25 g of the methylene chloride soluble extract obtained from the Example 2 was subjected to silica gel column chromatography (10×45 cm, Merck, ASTM 7734, German). The column was eluted with linear gradient using 1, 2, 3, 5, 10, 50 and 100% of chloroform-methanol solvent mixture to obtained 16 fractions. Among the 16 fractions, fraction 10 was subjected to silica gel column chromatography (3×10 cm, Merck, ASTM 7734, German) using as an eluent, a solvent mixture of hexane:ethylacetate with a ratio of 10:1, 8:5, 5:8 and 1:10 to obtain 50 mg of applanatic acid D having $R_f$ value of 0.41 on TLC using as an eluent, a solvent mixture of hexane:ethylacetate with a ratio of 1:10. Applanatic acid D, (20S,23R)-7β,20,23-trihydroxy-3,11,15-trioxolanosta-8-en-26-oic acid of the following chemical formula (X) was identified by using UV, IR, EI-Mass and NMR spectra (See Table 1) and was used as a sample in Experimental Example:

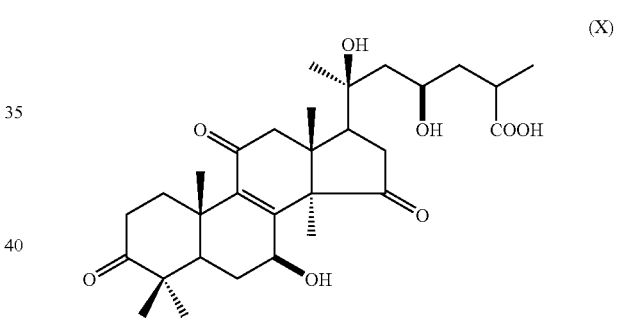

(X)

Melting point: 218-220° C. $[α]_D^{26}$=+225.5 (c=0.216, CHCl$_3$), UV λ$_{max}$ (methanol): 250 nm (log ε 4.07), IR γ$_{max}$: 3569, 3491 (OH), 1767 (five-membered ring C=O), 1734 (six-membered ring C=O), 1699 (COOH), 1661 (α,β-unsaturated C=O), 1458 ($CH_2$), 1377 ($CH_3$), 1171, 1069 (OH), 924 cm$^{-1}$, EI-MS m/z (rel. int., %): 468 [M-($2H_2O$+CO)]$^+$ (6.6), 175 [$C_8H_{15}O_4$, side chain (SC)]$^+$ (8.3), 157 [SC—$H_2O$]$^+$ (6.6), 99 (30.6), 69 (100), 55 (95.0), (+)-HR FAB MS m/z: 537.2807, calculation value [$C_{30}H_{42}O_7$Na (M+Na—$H_2O$)$^+$: 537.2862]

TABLE 1

| | NMR data for applanatic acids C and D in CDCl$_3$ | | | |
|---|---|---|---|---|
| Carbon | Applanatic acid C | | Applanatic acids D | |
| No. | δH$^{a)}$ | δC$^{b)}$ | δB$^{c)}$ | δC$^{b)}$ |
| 1 | 1.00 br d (10.0, 15.0) | 35.1 | 1.42-1.53 | 35.9 |
| | 2.86 m | | 2.95 ddd (5.4, 7.5, 13.7) | |
| 2 | 1.68 m | 28.0 | 2.4-2.6 | 34.5 |
| 3 | 3.23 dd (5.5, 11.0) | 78.6 | — | 216.8 |
| 4 | — | 39.1 | — | 47.0 |

TABLE 1-continued

NMR data for applanatic acids C and D in CDCl$_3$

| Carbon No. | Applanatic acid C | | Applanatic acids D | |
|---|---|---|---|---|
| | $\delta H^{a)}$ | $\delta C^{b)}$ | $\delta B^{c)}$ | $\delta C^{b)}$ |
| 5 | 0.89 dd (1.0, 13.0) | 49.4 | 1.58 dd (1.0, 12.8) | 49.2 |
| 6 | 2.21 ddd (1.5, 8.0, 13.0) 1.63 ddd (2.5, 6.5, 13.0) | 26.9 | 2.12 ddd (1.2, 7.8, 13.5) 1.70 dd (9.6, 13.5) | 27.9 |
| 7 | 4.81 dd (8.0, 9.0) | 67.1 | 4.85 m | 66.5 |
| 8 | — | 156.9 | — | 157.9 |
| 9 | — | 142.7 | — | 141.3 |
| 10 | — | 38.9 | — | 38.5 |
| 11 | — | 198.0 | — | 197.8 |
| 12 | 2.79 d (17.4) 2.86 d (17.4) | 51.1 | 2.78 d (17.4) 2.87 d (17.4) | 50.9 |
| 13 | — | 46.0 | — | 45.7 |
| 14 | — | 59.8 | — | 59.8 |
| 15 | — | 217.9 | — | 218.0 |
| 16 | 2.57 dd (8.0, 19.5) 2.81 dd (10.0, 19.5) | 36.2 | 2.56 dd (8.4, 19.5) 2.82 dd (10.5, 19.5) | 36.4 |
| 17 | 2.27 dd (8.0, 10.0) | 50.2 | 2.24 dd (9.0, 9.6) | 50.4 |
| 18 | 1.17 s | 19.1 | 1.18 s | 19.4 |
| 19 | 1.24 s | 18.6 | 1.26 s | 18.4 |
| 20 | — | 73.4 | — | 73.3 |
| 21 | 1.47 s | 26.4 | 1.46 s | 26.3 |
| 22 | 1.68 m 1.90 dd (10.5, 14.5) | 48.5 | 1.65 dd (2.4, 14.7) 1.88 dd (10.5, 14.7) | 48.5 |
| 23 | 4.85 ddd (4.0, 6.5, 8.5) | 74.8 | 4.82 m | 74.8 |
| 24 | 2.10 dd (6.5, 7.5) | 36.8 | 20.8 dd (6.6, 7.8) | 36.8 |
| 25 | 2.72 dd (7.5, 15.5) | 33.8 | 2.70 dd (7.2, 15.3) | 33.7 |
| 26 | — | 178.8 | — | 178.8 |
| 27 | 1.33 d (7.5) | 16.1 | 1.31 d (7.2) | 16.1 |
| 28 | 1.06 s | 28.4 | 1.12 s | 27.2 |
| 29 | 0.87 s | 15.7 | 1.10 s | 21.0 |
| 30 | 1.36 s | 25.1 | 1.34 s | 25.3 |

$^{a)}$500 MHz,
$^{b)}$125 MHz,
$^{c)}$300 MHz.

EXPERIMENTAL EXAMPLE 1

Inhibitory Effect of *Elfvingia applanata* Extracts on Aldose Reductase Activity In Vitro (1) Preparation of Aldose Reductase Crude aldose reductase (AR) was prepared as follows: rat lense were removed from SD rats weighing 250-280 g and frozen until use. The supernatant fraction of the rat lens homogenate was prepared in accordance with the procedure described in literature (Hayman, S. & Kinoshita, J. H.; *J. Biol. Chem.*, 240, pp 877-882, 1965). Partially purified enzyme with a specific activity of 6.5 U/mg was routinely used to rest enzyme inhibition.

(2) Measurement of Aldose Reductase Activity AR activity was assayed spectrophotometrically by measuring the decrease in absorption of NADPH at 340 nm over a 5 min with DL-glyceraldehyde as a substrate (Sato, S and Kador, P. F., *Biochem. Pharmacol.*, 40, pp 1033-1042, 1990). Each 1.0 ml of cuvette containing equal units of enzyme, 0.10M sodium phospate buffer (pH 6.2), 0.3 mM NADPH with or without 10 mM substrate and the enzyme inhibitor. The concentration of inhibitors giving 50% inhibition of enzyme activity ($IC_{50}$) was calculated from the lease-squares regression line of the logarithmic concentration plotted against the remaining activity.

As can be seen in Table 2, the inventive extract, fractions and compounds of *Elfvingia applanata* showed potent inhibitory effect on aldose reductase activity in vitro. Also, comparing with that of positive control group, tetramethylene glutaric acid (TMG), the extract, fractions theseof and the compounds of the present invention showed more significant inhibitory effect on aldose reductase activity.

TABLE 2

Inhibitory effect of *Elfvingia applanata* extracts on rat lenses aldose reductase activity.

| Sample | Concentration | inhibition (%) | $IC_{50}$(μg/ml) |
|---|---|---|---|
| TMG | 10 | 82.1 | 0.63 |
| | 1 | 53.7 | |
| | 0.1 | 29.8 | |
| n-hexane soluble extract | 100 | 91.1 | 4.98 |
| | 10 | 52.7 | |
| | 1 | 32.7 | |
| Methylene chloride soluble extract | 10 | 87.2 | 1.66 |
| | 5 | 68.2 | |
| | 1 | 41.2 | |
| Ethylacetate soluble extract | 100 | 100 | 0.66 |
| | 10 | 90.5 | |
| | 1 | 66.6 | |
| | 0.5 | 37.7 | |
| Butanol soluble extract | 10 | 94.4 | 1.29 |
| | 1 | 37.7 | |
| | 0.5 | 35.4 | |
| Polyphenol fraction A | 100 | 97.4 | 0.89 |
| | 10 | 81.2 | |
| | 1 | 48.5 | |
| Polyphenol fraction B | 100 | 89.0 | 11.7 |
| | 10 | 51.4 | |
| | 1 | 30.8 | |

TABLE 2-continued

Inhibitory effect of *Elfvingia applanata* extracts on rat lenses aldose reductase activity.

| Sample | Concentration | inhibition (%) | IC$_{50}$(μg/ml) |
|---|---|---|---|
| Polyphenol fraction C | 100 | 99.2 | 0.73 |
| | 10 | 86.4 | |
| | 1 | 49.4 | |
| Polyphenol fraction D | 100 | 97.0 | 2.0 |
| | 10 | 62.6 | |
| | 1 | 45.0 | |
| 2,5-dihydroxybenzoic acid | 100 | 0 | 39.4 |
| | 50 | 83.16 | |
| | 10 | 53.45 | |
| Protocatechualdehyde | 100 | 100 | |
| | 10 | 96.7 | 0.72 |
| | 5 | 85.0 | |
| | 1 | 39.7 | |
| Cerebroside | 100 | 6.85 | 30.0 |
| | 50 | 94.27 | |
| | 10 | 66.31 | |
| 5-dihydroergosterol | 100 | 18.90 | |
| 2-methoxyfatty acid | 100 | 20.73 | |
| Cerevisterol | 100 | 40.3 | |
| Applanatic acid C | 100 | 30.05 | |
| Applanatic acid D | 100 | 25.19 | |

Inhibition rate was calculated as the percentage with respect to that of the control value.
TMG*: abbreviation of TetraMethylene Glutaric acid.

EXPERIMENTAL EXAMPLE 2

Cytotoxicity Tests

The cytotoxicity of the extract, the fractions and the compounds isolated from *Elfvingia applanata* were tested by the procedure described as below.

The toxicity tests on ICR mice and Sprague-Dawley rats were performed using the extract, the fractions and the compounds of the present invention. Each group consisting of 3 mice or rats was administrated intraperitoneally with 20 mg/kg, 10 mg/kg and 1 mg/kg of the extracts and compounds of present invention, respectively and observed for 24 hrs.

There were no treatment-related effects on mortality, clinical signs, body weight changes and gross findings in any group or either gender. These results suggested that the compounds of the present invention were potent and safe.

Hereinafter, the formulating methods and kinds of excipients will be described, but the present invention is not limited to them. The representative preparation examples were described as follows.

| Preparation of powder | |
|---|---|
| Polyphenol fraction A | 100 mg |
| Corn Starch | 100 mg |
| Lactose | 100 mg |
| Talc | 10 mg |

Powder preparation was prepared by mixing above components and filling sealed package.

| Preparation of tablet | |
|---|---|
| 2,5-dihydroxybenzoic acid | 100 mg |
| Corn Starch | 100 mg |
| Lactose | 100 mg |
| Magnesium stearate | 2 mg |

Tablet preparation was prepared by mixing above components and entabletting.

| Preparation of capsule | |
|---|---|
| Protocatechualdehyde | 100 mg |
| Lactose | 50 mg |
| Magnesium stearate | 1 mg |

Tablet preparation was prepared by mixing above components and filling gelatin capsule by conventional gelatin preparation method.

| Preparation of liquid | |
|---|---|
| applanatic acid D | 100 mg |
| Sugar | 10 g |
| Polysaccharide | 10 g |
| Lemon flavor | optimum amount |
| Distilled water | optimum amount |

Liquid preparation was prepared by dissolving active component, and then filling all the components in 100 ml ample and sterilizing by conventional liquid preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

As mentioned above, since inventive non-polar solvent soluble extract, polyphenol fractions thereof and the compounds isolated from *Elfvingia applanata* showed various activity to inhibit aldose reductase activity, it can be used as pharmaceutical composition not only to prevent or treat diabetes but also to inhibit diabetic complications.

While the invention has been described with respect to the above specific embodiments, it should be recognized that various modifications and changes may be made to the invention by those skilled in the art which also fall within the scope of the invention as defined by the appended claims.

The invention claimed is:

1. An applanatic acid derivative compound having the chemical formula (VIII):

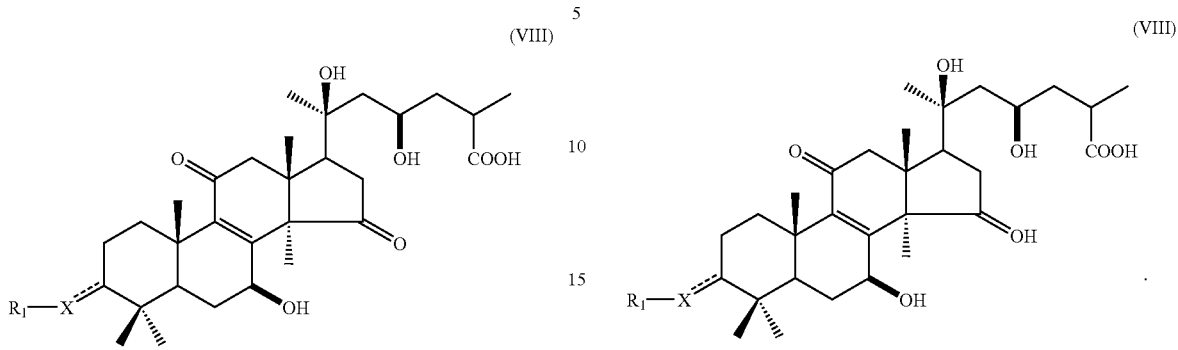
(VIII)

Wherein,
X is an oxygen, sulfur or nitrogen atom;
R₁ is a hydrogen or an alkyl group of 1 to 4 carbon atoms or is absent; and
----- is a single bond or double bond; or a pharmaceutically acceptable salt or isomer of said compound.

2. The compound of claim 1 wherein said compound is applanatic acid C having the chemical formula (IX):

(IX)

3. The compound of claim 1 wherein said compound is applanatic acid D having the chemical formula (X):

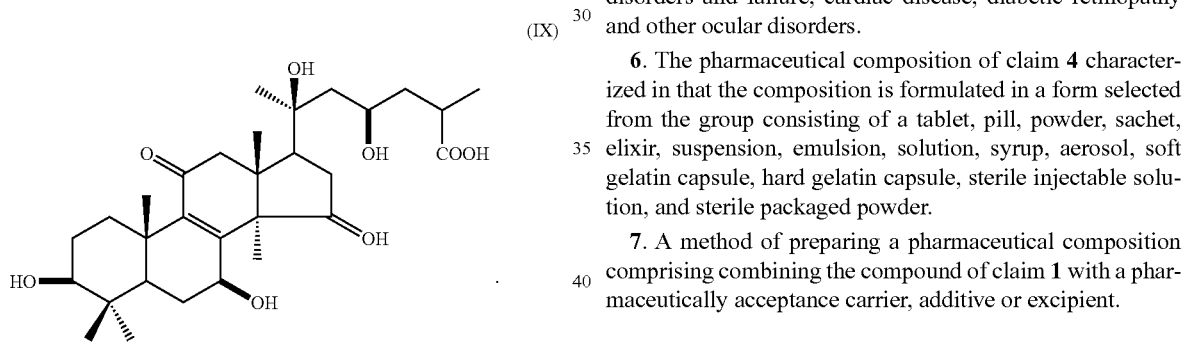
(VIII)

4. A pharmaceutical composition for the treatment of diabetes and diabetic complications comprising the compound of claim 1 as an effective component, or in combination with a pharmaceutically acceptable carrier, additive or excipient.

5. The pharmaceutical composition of claim 4 wherein the diabetic complication is selected from the group consisting of hyperglycemia, atherosclerosis, microangiopathy, kidney disorders and failure, cardiac disease, diabetic retinopathy and other ocular disorders.

6. The pharmaceutical composition of claim 4 characterized in that the composition is formulated in a form selected from the group consisting of a tablet, pill, powder, sachet, elixir, suspension, emulsion, solution, syrup, aerosol, soft gelatin capsule, hard gelatin capsule, sterile injectable solution, and sterile packaged powder.

7. A method of preparing a pharmaceutical composition comprising combining the compound of claim 1 with a pharmaceutically acceptance carrier, additive or excipient.

* * * * *